United States Patent [19]

Wenmaekers

[11] 4,124,720

[45] Nov. 7, 1978

[54] THERAPEUTIC HYDRODISPERSIBLE EMULSION

[76] Inventor: Georges E. J. Wenmaekers, 23, rue du Général Chanzy, 94, Nogent-sur-Marne, France

[21] Appl. No.: 664,670

[22] Filed: Mar. 8, 1976

Related U.S. Application Data

[63] Continuation of Ser. No. 481,758, Jun. 21, 1974, abandoned, which is a continuation of Ser. No. 196,745, Nov. 8, 1971, abandoned.

[30] Foreign Application Priority Data

Nov. 9, 1970 [FR] France .................................. 70 40221

[51] Int. Cl.² .............................................. A61K 31/335; A61K 31/56; A61K 31/23
[52] U.S. Cl. .................................... 424/278; 424/240; 424/312; 424/347; 424/365;
[58] Field of Search ................ 424/312, 365, 240, 278, 424/347

[56] References Cited

U.S. PATENT DOCUMENTS

| | | | |
|---|---|---|---|
| 1,979,385 | 11/1934 | Harvey | 424/365 |
| 2,114,370 | 4/1938 | Bikenheuser | 424/365 |
| 2,129,836 | 9/1938 | Goodman | 424/365 |
| 2,172,118 | 9/1939 | Blish | 424/361 |
| 3,211,618 | 10/1965 | Kambersky | 424/365 |

*Primary Examiner*—Sam Rosen

[57] ABSTRACT

The disclosure relates to a therapeutic oil in water emulsion, wherein the dispersed phase comprises 5 to 20% by weight of fatty acids, 1 to 30% by weight of an emulsifying agent, 2 to 40% by weight of wetting agents, 0.1 to 5% by weight of a protective colloid, 0 to 60% by weight of waxes and oils, and a base in amount sufficient to always maintain the pH in the vicinity of 6.2.

19 Claims, No Drawings

THERAPEUTIC HYDRODISPERSIBLE EMULSION

CROSS REFERENCE TO RELATED APPLICATIONS

This is a continuation of application Ser. No. 481,758, filed June 21, 1974, now abandoned, which in turn is a continuation of copending application Ser. No. 196,745, filed Nov. 8, 1971, also abandoned.

The present invention is directed to a composition which is in the form of a hydrodispersible emulsion, and which possesses new therapeutical properties.

Antalgic treatments or treatments intended for accelerated healing are usually carried out by applying cooling, simple fatty materials, calcareous materials, anaesthetics, picric acid, preparations containing antiseptic agents, fungicides, antibiotics, or corticoidic agents to the wounded area of the body. These treatments are difficult and/or are not easy for the patient.

For example, in a mycosis which is often complicated with inflammation resulting from scratching, the proposed treatments are insufficient, can be painful, and are unpleasant because of the smell. In addition, the compositions used for these treatments are often fatty and sticky.

I have discovered that the above disadvantages can be overcome, or at least mitigated, by using as treatment a composition which is in the form of a hydrodispersible emulsion and is characterized by the fact that it comprises 5 to 20% by weight of fatty acids, 1 to 30% by weight of an emulsifying agent, 2 to 20% by weight of a wetting agent, 0.1 to 5% by weight of a protective colloid, 0 to 60% by weight of waxes and oils, and a base in amount sufficient to maintain the pH always in the vicinity of 6.2

Preferably, the fatty acids will consist of stearin, (i.e., commercial grade stearic acid) and the base will be triethanolamine or isopropanolamine, the latter being used to give products having more body. The base should be used in such quantity that the pH of the emulsion will be 6.2, such pH being recommended for the care of the skin.

On the other hand, the emulsifying agent could be selected from among the numerous products available on the market; it could for example be glycol monostearate.

The wetting agent may comprise glycerine or various glycols, preferably propanediol-1,2.

Among the waxes which will be used for forming the composition in accordance with my invention, solid paraffin and hexadecanol are preferred.

The oils may include mineral oils, oils derived from fish or vegetable oils. The preferred mineral oil is liquid paraffin. The recommended fish oils include oils extracted from shark or squale livers. The preferred vegetable oil is avocado oil.

Any of the available protective colloids can be used, however, I prefer to use sodium alginate or more preferably triethanolamine alginate in order to obtain a cream with a viscosity of 10 to 3,000 centipoises, preferably 140 to 170.

An example of a suitable emulsifiable composition is one having the following composition:
Fatty acid:15% by weight
Emulsifying agent:23% by weight
Wetting agent:10% by weight
Protective colloid:3% by weight
Waxes and oils:49% by weight In accordance with another aspect of my invention, the addition of an antiseptic agent, and/or a bactericide, and/or a bactericide-fungicide agent, and/or a bacteriostatic agent, and/or an antibiotic and/or a corticosteroid may in certain cases, give added properties to the mixture, in addition to the specific action which is expected. These agents can be added alone or in any combination depending on circumstances and the results which are desired.

The composition can be used for skin care in the form of a paste, a cream, a milk or a lotion, becuase it possesses antalgic properties and in view of the fact that it can accelerate healing. For example, the composition can be used for treating insect bites, wounds or burns.

The addition of an antiseptic agent and a fungicide agent may serve to preserve the composition. Among these agents, hexachlorophene is preferred. The concentration of this agent, can vary between 0.1 to 2% by weight of the weight of the composition, preferably about 1.5% by weight.

In order to further improve the composition, a bacteriostatic agent can be added for the purpose of treating more diseases. For this purpose, 6-acetoxy-3,4-dimethyl-dioxane ($C_8H_{14}O_4$) has been selected for its noted physical properties. However, I do not wish to be restricted to this particular bacteriostatic agent. The solubility of this compound in water and in oil is particularly suitable for producing an emulsion of water in oil. When preparing the composition, the bacteriostatic agent can be diluted in a mixture comprising water and a colloidal agent at the rate of 0.01% to 1% of solid matter, preferably 0.08% by weight.

The production of a composition in which the consistency can vary from a paste to a lotion, via a cream or a milk, can be obtained by varying the proportion of water and/or by selecting the viscosity of the colloidal agent. In the case of a cream, I use 3.2 parts of soft water for 1 part of solid matter, i.e., about 75% water.

In order to better illustrate the invention, I will now describe one example by way of illustration and without restriction.

EXAMPLE

There are used 3.2 parts of water for 1 part of the composition, the latter comprising the following mixture:
Fatty acid:15% by weight
Emulsifying agent:23% by weight
Wetting agent:10% by weight
Protective colloid:3% by weight
Waxes and oils:49% by weight 2.5 parts of water and the oil consisting of liquid paraffin are heated to 100° C. The protective colloid is dispersed in the remaining portion of water. Hexachlorophene is thereafter diluted with the wetting agent. The fatty acid, the emulsifying agent and the waxes are then heated to 80° C. The oils, and the mixture comprising the wetting agent and the hexachlorophene mentioned above are thereafter poured into the mixture of fatty acid, emulsifying agent, and waxes heated to 80° C. and the oils are thereafter filtered. The mixture of water and of liquid paraffin is cooled down to 80° C., a base is added and mixing is carried out during 30 seconds. This mixture is rapidly poured into the filtered oil and is strongly mixed. It is then allowed to be cooled under cover and while regularly mixing until the temperature reaches 60° C. About 1/10th of this mixture is poured and mixed in the mixture made of the colloid which is dispersed in the remaining portion of water, then a second 1/10th of the mixture is added and mixed. The whole can thereafter be combined and suitably mixed.

The composition according to the invention can be used as medicine in hospitals and as prescription drugs for patients at home. It can be used for treating persons suffering from burns, those who have been operated on and those involved in accidents. It can also be used as antalgic agent for curing wounds by accelerating the healing and for treating dermatosis and mycosis.

Repeated uses of the composition according to the invention will remove the pain, and will contribute to a fast regeneration of the damaged skin, all this being accompanied by a beneficial effect, even for a healthy skin in the vicinity of the area under treatment.

Clinical observations have established that slight burns, which are painful and accompanied with blisters, will require many days before healing and can cause the loss of many working hours. When these burns are treated with the composition of the present invention, the burns will disappear in the following hour without any pain; and if any pain subsists, it will disappear even if application of the complex has been delayed. After a few hours, all red spots will disappear. The same results can be observed after treating sun burns and burns suffered at home or at work.

In the case of serious burns, the pain is considerably weakened as soon as the composition is applied, healing is strongly accelerated. This treatment contributes to a normal rebuilding of the skin, without random healing.

If a strong pain reappears, a new application will be made over the one which has been absorbed, resulting in a sensation of freshness; the pain will also disappear.

Another property of the composition is to remove itching which will reduce scratching of scabs at the end of the healing period. In serious cases, it will be noted that there will be no secondary injuries to the portion of the skin which is less seriously attacked; and it will be noticed that there will be a rapid regeneration of the skin.

I claim:
1. A therapeutic composition in the form of an aqueous emulsion, for local application to the skin in the prevention and treatment of cutaneous thermal burns, which comprises about 75% by weight of water and about 25% by weight of a mixture of the following ingredients, on dry basis:
 a. 5 to 20% by weight of stearic acid;
 b. 1 to 30% by weight of an emulsifying agent;
 c. 2 to 40% by weight of a wetting agent;
 d. 0.1 to 5% by weight of sodium alginate as a protective colloid;
 e. 0 to 60% by weight of waxes and oils; and
 f. an organic base consisting of triethanolamine to provide an emulsion having a pH in the vicinity of 6.2.

2. The composition of claim 1, wherein the emulsifying agent is glycol monostearate.
3. The composition of claim 1, wherein the wetting agent is propanediol-1,2.
4. The composition of claim 1, wherein the waxes are selected from the group consisting of hard paraffin and hexadecanol.
5. The composition of claim 1, wherein the oils are selected from the group consisting of mineral oils, fish oils and vegetable oils.
6. The composition of claim 5, wherein the mineral oil is liquid paraffin.
7. The composition of claim 5, wherein the fish oil is squalene oil.
8. The composition of claim 5, wherein the vegetable oil is avocado oil.
9. The composition of claim 1, wherein the mixture includes an antiseptic agent, a bactericide-fungicide agent, a bacteriostatic agent, an antibiotic or a corticosteroid, or a mixture thereof.
10. The composition of claim 9, wherein the bactericide-fungicide agent is present in an amount of 0.1 to 2% by weight.
11. The composition of claim 10, wherein the bactericide-fungicide agent is hexachlorophene.
12. The composition of claim 9, wherein the bacteriostatic agent is present in an amount of 0.01 to 1% by weight.
13. The composition of claim 12, wherein the bacteriostatic agent is 6-acetoxy-3,4-dimethyl-dioxane.
14. The composition of claim 1, wherein the mixture includes 15% by weight of stearic acid, 23% by weight of the emulsifying agent, 10% by weight of the wetting agent, 3% by weight of the protective colloid and 49% by weight of the waxes and oils.
15. The composition of claim 14, wherein the emulsifying agent is glycol monostearate, the wetting agent is propane-diol, and the waxes and oils are solid paraffin, hexadecanol, liquid paraffin, squalene oil or avocado oil.
16. A method of treating a burn on a patient suffering from burns which comprises applying to the burn the composition of claim 1.
17. A therapeutic oil in water emulsion containing about 75% water and a dispersed phase which comprises, on a dry weight basis;
 a. 5 to 20% by weight of stearic acid;
 b. 1 to 30% by weight an emulsifying agent;
 c. 2 to 40% by weight of a wetting agent; and
 d. 0.1 to 5% by weight of a protective colloid which is an alginate, said emulsion having a pH in the vicinity of 6.2
18. The composition of claim 17, wherein the alginate is sodium alginate or triethanolamine alginate.
19. A method of treating burns on a patient suffering from burns which comprises repeatedly applying to the burns the composition of claim 17.

* * * * *